US010561376B1

(12) United States Patent
Kahn et al.

(10) Patent No.: US 10,561,376 B1
(45) Date of Patent: Feb. 18, 2020

(54) METHOD AND APPARATUS TO USE A SENSOR IN A BODY-WORN DEVICE (71) Applicants: Philippe Kahn, Santa Cruz, CA (US); Arthur Kinsolving, Santa Cruz, CA (US)

(72) Inventors: Philippe Kahn, Santa Cruz, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 675 days.

(21) Appl. No.: 13/666,929

(22) Filed: Nov. 1, 2012

Related U.S. Application Data (60) Provisional application No. 61/555,426, filed on Nov. 3, 2011.

(51) Int. Cl.
*A61B 5/00* (2006.01)

(52) U.S. Cl.
CPC ............ *A61B 5/746* (2013.01); *A61B 5/441* (2013.01); *A61B 5/4806* (2013.01); *A61B 5/681* (2013.01)

(58) Field of Classification Search
CPC ........... G01J 1/429; G02C 5/001; G06N 5/00; A61B 5/746; A61B 5/441; A61B 5/4806; A61B 5/4812; A61B 5/681; A61B 5/7275
USPC ......................................................... 250/372
See application file for complete search history.

(56) References Cited

U.S. PATENT DOCUMENTS

| 5,928,133 | A | 7/1999 | Halyak |
| 6,348,694 | B1* | 2/2002 | Gershteyn ............ A61B 5/0059 250/372 |
| 6,888,779 | B2 | 5/2005 | Mollicone et al. |
| 8,398,546 | B2 | 3/2013 | Pacione et al. |
| 8,770,742 | B2 | 7/2014 | Howell |
| 8,793,212 | B2* | 7/2014 | McGuire ........................ 706/62 |
| 8,840,564 | B2 | 9/2014 | Pinhas et al. |
| 9,192,326 | B2 | 11/2015 | Kahn |
| 2004/0049132 | A1 | 3/2004 | Barron et al. |
| 2004/0075549 | A1 | 4/2004 | Haller |
| 2004/0133081 | A1 | 7/2004 | Teller et al. |
| 2004/0149921 | A1* | 8/2004 | Smyk ........................... 250/372 |
| 2004/0152957 | A1 | 8/2004 | Stivoric et al. |

(Continued)

FOREIGN PATENT DOCUMENTS

| EP | 1139187 B1 | 10/2001 |
| WO | WO 2005/092177 | 10/2005 |

(Continued)

OTHER PUBLICATIONS

"Control of skin cancer by the circadian rhythm", PNAS, vol. 108, No. 46, pp. 18790-18795, Nov. 2011 to Shelby et al.*

(Continued)

*Primary Examiner* — Kenneth J Malkowski
(74) *Attorney, Agent, or Firm* — HIPLegal LLP; Judith Szepesi (57) ABSTRACT

A body-worn device comprising a radiation system to determine a raw radiation exposure of a user, and a user characteristic adjustment logic to adjust the raw radiation exposure based on user characteristics is described. The body-worn device in one embodiment further includes a recommendation calculator to determine a recommendation to the user, based on the adjusted radiation exposure.

12 Claims, 9 Drawing Sheets

(56) References Cited

U.S. PATENT DOCUMENTS

| | | |
|---|---|---|
| 2005/0143617 A1 | 6/2005 | Auphan |
| 2005/0154330 A1 | 7/2005 | Loree |
| 2005/0172311 A1 | 8/2005 | Hjelt et al. |
| 2005/0245839 A1 | 11/2005 | Stivoric et al. |
| 2005/0264752 A1* | 12/2005 | Howell .................. G02C 5/001 351/41 |
| 2006/0202816 A1 | 9/2006 | Crump et al. |
| 2006/0293608 A1 | 12/2006 | Rothman et al. |
| 2007/0018832 A1 | 1/2007 | Beigel et al. |
| 2007/0186330 A1 | 8/2007 | Howell et al. |
| 2008/0052837 A1 | 3/2008 | Blumberg |
| 2008/0117060 A1 | 5/2008 | Cuddihy et al. |
| 2008/0122616 A1 | 5/2008 | Warner et al. |
| 2008/0234785 A1 | 9/2008 | Nakayama et al. |
| 2008/0234935 A1 | 9/2008 | Wolf et al. |
| 2008/0275349 A1 | 11/2008 | Halperin et al. |
| 2008/0306351 A1 | 12/2008 | Izumi |
| 2009/0069642 A1 | 3/2009 | Gao et al. |
| 2009/0147215 A1* | 6/2009 | Howell et al. ................ 351/158 |
| 2009/0203971 A1 | 8/2009 | Sciarappa et al. |
| 2010/0049008 A1 | 2/2010 | Doherty et al. |
| 2010/0056947 A1 | 3/2010 | Holmes |
| 2010/0079294 A1 | 4/2010 | Rai et al. |
| 2010/0100004 A1 | 4/2010 | Someren |
| 2010/0283616 A1 | 11/2010 | Ruhs et al. |
| 2010/0306711 A1 | 12/2010 | Kahn et al. |
| 2011/0010014 A1 | 1/2011 | Oexman et al. |
| 2011/0015467 A1 | 1/2011 | Dothie et al. |
| 2011/0015495 A1 | 1/2011 | Dothie et al. |
| 2011/0092780 A1 | 4/2011 | Zhang et al. |
| 2011/0152637 A1 | 6/2011 | Kateraas et al. |
| 2011/0190594 A1 | 8/2011 | Heit et al. |
| 2011/0270052 A1 | 11/2011 | Jensen et al. |
| 2011/0298613 A1 | 12/2011 | Ayed |
| 2012/0103556 A1 | 5/2012 | Lee |
| 2012/0313272 A1 | 12/2012 | Fullam et al. |
| 2012/0316932 A1 | 12/2012 | Rahman et al. |
| 2012/0317430 A1 | 12/2012 | Rahman et al. |
| 2013/0018284 A1 | 1/2013 | Kahn et al. |
| 2013/0072765 A1 | 3/2013 | Kahn et al. |
| 2013/0124891 A1 | 5/2013 | Donaldson |
| 2014/0018686 A1 | 1/2014 | Medelius et al. |
| 2014/0259433 A1 | 9/2014 | Nunn et al. |
| 2014/0277822 A1 | 9/2014 | Nunn et al. |
| 2015/0083934 A1 | 3/2015 | Richter |

FOREIGN PATENT DOCUMENTS

| | | |
|---|---|---|
| WO | WO 2006/009830 | 1/2006 |
| WO | WO 2008/072168 | 6/2008 |
| WO | 2011161680 A2 | 12/2011 |

OTHER PUBLICATIONS

"SunMate Ultraviolet Light Intensity Meter," <http://www.natures-energies.com/uv_meter.htm#.UlpCP44qe-ghat>, Accessed Oct. 26, 2012, 1 page.

"UV Sunsignals Sensors," <http://sunsignals.com/how-it-works/> Accessed Oct. 26, 2012, 2 pages.

Coyle, Shirley, et al, "Textile Sensors to Measure Sweat pH and Sweat-rate During Exercise," <http://doras.dcu.ie/3636/1/Coyle_pervasive2009.pdf>, Accessed Sep. 12, 2012, 6 pages.

"Direct Link Between Insulin, Core Body Temperature Discovered," Thaindian News, <http://www.thaindian.com/newsportal/health/direct-link-between-insulin-core-body-temperature-discovered_100277502.html>,Nov. 20, 2009, 3 pages.

"Metabolic Temperature Graph," Dr. Rind, <http://www.drrind.com/therapies/metabolic-temperature-graph>, Accessed Sep. 18, 2012, 5 pages.

"Monitoring Disparities in Chronic Conditions Study: The MDCC Study," <http://www.healthmetricsandevaluation.org/research/project/monitoring-disparities-chronic-conditions-study-mdcc-study>, Accessed Sep. 7, 2012, 2 pages.

Iber, Conrad et al; The AASM manual for the Scoring of Sleep and Associated Events: Rules, Terminology and technical Specification, 1st ed., 2007 American Academy of Sleep medicine, Westchester, Illinois.

Plarre et al., "Automated Detection of Sensor Detachments for Physiological Sensing in the Wild", Wireless Health, Oct. 10, 2010, pp. 5-7.

* cited by examiner

METHOD AND APPARATUS TO USE A SENSOR IN A BODY-WORN DEVICE

RELATED CASES

The present invention claims priority to U.S. Provisional Application Ser. No. 61/555,426, filed on Nov. 3, 2011, which is incorporated herein in its entirety.

FIELD

The present invention relates to body-worn devices, and more particularly to the uses of a sensor in a body worn device.

BACKGROUND

Over-exposure to the sun can not only cause temporary issues such as sun burn and drying skin, it can increase the risk of longer-term problems including skin cancer and wrinkling. There are numerous rules and goals for users to follow, in limiting excessive sun exposure.

In the prior art, there are ultraviolet intensity meters. One prior art mechanism measures the UV intensity, and indicates the current ultraviolet index, from "no danger" to "extreme risk of harm." One prior art mechanism is an article of clothing, such as a hat, which includes a radiation sensor. The hat's radiation sensor has a simple user interface output, which communicates the overall UV radiation exposure to a user via a display.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A body-worn device including one or more sensors is described. In one embodiment, a sensor may be a radiation sensor or light sensor. The sensor may be used, in one embodiment, to determine when the user is exposed to UV radiation, and determine and inform the user of cancer risk, and/or other health risks. It is known that for certain conditions sun exposure is helpful, e.g. for depression, sufficient Vitamin-D availability, etc. It is also known that excess sun exposure can lead to sunburns, sunstroke, skin cancer, and other health issues. In one embodiment, cosmetic results of sun exposure, such as tanning and wrinkles may also be monitored. Therefore, in one embodiment, the sensor, optionally in combination with other sensors, is used to ensure that the user receives adequate sun exposure, but avoids excessive sun exposure. In one embodiment, additional sensors may also be used to monitor the user's health and condition, and to make recommendations to the user. In one embodiment, the sensors may be coupled to the body-worn device through an interface, rather than being directly part of the body-worn device.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

Figure 1:
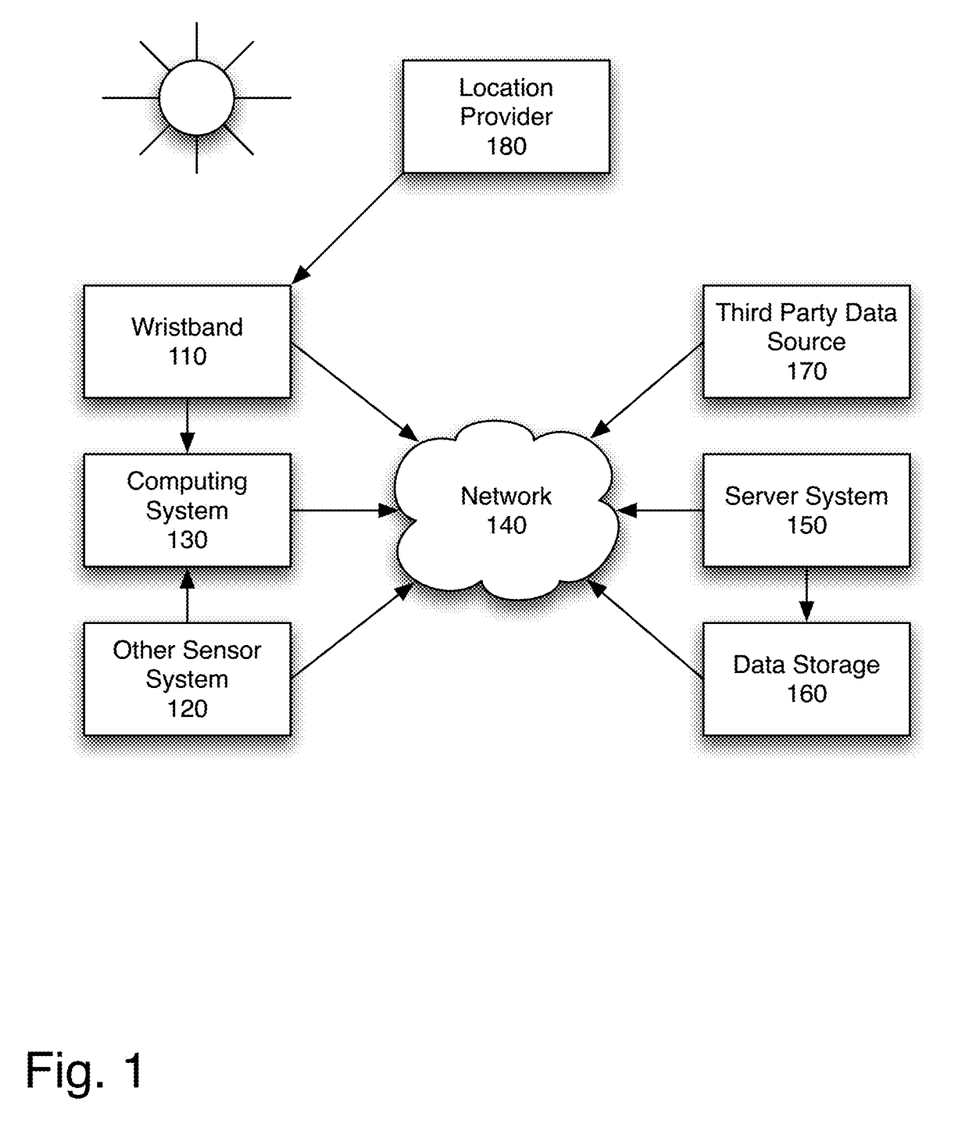
FIG. 1 is a diagram of one embodiment of an environment in which a wristband or other mobile sensing device may be used.

FIG. 1 is a diagram of one embodiment of a wristband that may include the present invention. Although the term wristband is used in the Specification, the body-worn device may also be embodied in a different device 120, which may be a watch, a mobile telephone, an armband, a hat, eyeglasses, or another format in which the device is exposed to the elements, and worn by the user.

The wristband 110, in one embodiment, includes a radiation and/or light sensor, disposed on the wristband 110 such that when the wristband is worn, the sensor is exposed to the environment.

The wristband 110 may also include a mechanism to connect to a network 140, such as a wireless network connection or a cellular network connection. In on embodiment, the wristband 110 may connect to a computing system 130, which in turn connects to network 140. Computing system 130 may be a local mobile device or non-mobile device, which may be used to provide additional processing power, network connection features, and/or other features to wristband 110.

In one embodiment, wristband 110 may alternately, or additionally, include a physical connection mechanism to connect to computing system 130. One embodiment of the physical connection mechanism is a connection port, such as a USB (universal serial port), micro-USB, Thunderbolt connector, Lightning connector, or one of the many similar small format connectors. In one embodiment, the physical connection mechanism is a headset port. The physical connection an then be established using a cable having an end which fits into the connection port or the headset port of the wristband, and into a USB port, or other appropriate port on the computing system 130.

The wristband 110 may also connect to location provider 180. The location provider 180 may be a set of GPS satellites, one or more network base stations, cellular antennas, or another system that may be used by the wristband 110 to obtain location information.

Although the user-side system is described as a wristband 110, it may be another sensor system 120, as noted above. In one embodiment, a wristband 110 may interact with another sensor system 120, for example a mobile telephone or similar device also carried by the user. In one embodiment, a subset of functionality may be provided by each of the wristband 110 and sensor system 120, such that the complete data, described below is obtained by merging data from the wristband 110 and other sensor system 120.

The wristband 110 may further interact with server system 150. Server system 150 may store data in local, remote, or distributed data storage 160. The data may include user identifiable data, in one embodiment. In another embodiment, only aggregate data is stored in data storage 160, and user identifiable data is stored on computing system 130. In one embodiment, third party data source 170 may be used to obtain additional information. Third party data sources 170 may provide statistical data, weather data, radiation level data, genetic data, and/or other data, which may be used by the system.

Note that while wristband 110, sensor system 120, computing system 130, and server 150 are described separately, in one embodiment, the processing, and other features described below may be split between these devices in various ways. For example, the wristband 110 may simply include one or more sensors or sensor interfaces, memory, and the ability to provide the data to sensor system 120 and/or computing system 130. Computing system 130 may locally process and analyze this data. Computing system 130 may further interact with server system 150. In one embodiment, computing system 130 may be removed entirely. In one embodiment, server system 150 may be removed entirely. In one embodiment, wristband 110 may not interact with any other devices and may provide sensing and processing as well as input/output.

Figure 2:
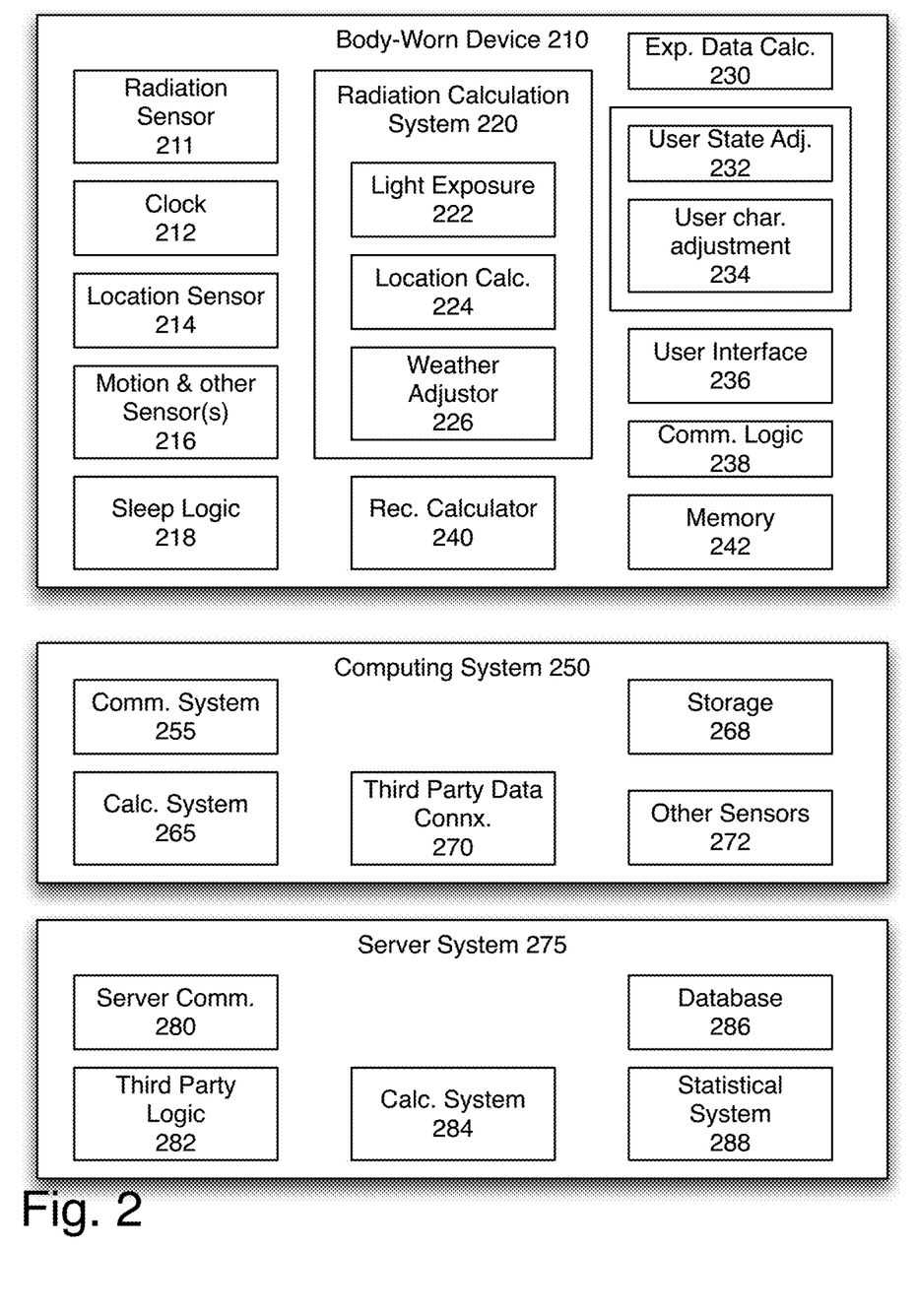
FIG. 2 is a block diagram of one embodiment of the system.

FIG. 2 is a block diagram of one embodiment of the system. The system, in one embodiment, includes a body-worn device 210, computing system 250, and server system 275. The body-worn device 210 may include a clock 212. The clock 212 may be a conventional clock based on a battery, a clock synchronized via a network connection, or a clock with atomic clock synchronization.

Although the system is illustrated in three segments, body-worn device 210, computing system 250, and server system 275, these three segments need not all be part of the system as a whole. Furthermore, functionality may be moved from one segment to another, or split between segments. The computing device 250 may be a mobile device, such as a smartphone, or another type of computing device.

The body-worn device 210 may include a radiation sensor 211, location sensor 214, motion and other sensors 216. These sensors may collect information. In one embodiment, the collected information is stored in memory 242. In one embodiment, sensor data is associated with a time and date stamp, provided by clock 212 in memory 242. In one embodiment, memory 242 may be a Flash memory. In one embodiment, instead of storing the data locally in memory 242, the data may be sent via communication logic 238 to computing system 250 and/or server system 275. In one embodiment, instead of storing the data, the system may first process the data and then store the result.

Sleep logic 218 may take data from the sensors, and potentially user input data (received via user interface 236 or via communication logic 238 from another device). Sleep logic 218 evaluates the user's sleep patterns, and makes recommendations based on the sleep patterns. In one embodiment, the techniques described in co-pending application U.S. Ser. No. 13/545,963, filed on 2012 Jul. 10, with the title "A Sleep Monitoring System," assigned to the assignee of this case, may be used for these recommendations. That application is incorporated herein by reference.

In one embodiment, radiation sensor 211 may be replaced by, or may co-exist with, radiation calculation system 220.

Radiation calculation system 220 may include light exposure sensor 222, location calculator 224, and weather adjustor 226. Radiation calculation system 220 can, based on data from light exposure sensor 222 and external data such as location and weather data, estimate radiation exposure.

Exposure data calculator 230 provides cumulative exposure calculations based on the data from the sensors. In one embodiment, effective exposure depends on measured/calculated radiation exposure, as adjusted by coverage adjustment 232 and user characteristic adjustment 234. In one embodiment, these adjustments may be made based on information received from the user via user interface 236. Effective exposure, as calculated by exposure data calculator 230 may further determine when the user has an over-exposure or under-exposure risk. This may then be used by user interface 236 to warn the user. Exposure data calculator 230 may be implemented in a processor, a digital signal processor (DSP), or other type of circuitry whether special purpose or general purpose.

In one embodiment, the user interface 236 may further be used to communicate recommendations to the user. Such recommendations are calculated by recommendation calculator 240, based on the information from exposure data calculator 230, and optionally additional sensor and external data. Memory 242 may further store user characteristic adjustment factors, as well as coverage adjustment factors. Additionally, memory 242 may store the information enabling the body-worn device 210 to communicate with the user.

Computing system 250 may be a local computing system to which body-worn device 210 may be coupled via a wireline connection, or a wireless connection. Computing system 250 includes a communications system 255, which enables it to communicate with body-worn device 210, and optionally server system 275.

Calculation system 265 provides calculations based on sensor data, effective exposure, and other factors. It allows the computing system 250 to provide more complex calculations than the body-worn device 210 based on the same sensor data, or augmented sensor data.

Storage 268 provides storage of the sensor data, and potentially recommendation and warning data in computing system 250. In one embodiment, body-worn device 210 keeps only a relatively short period of data, because of memory limitations. Computing system 250 may keep historical data, or complete data.

The computing system 250 may also include other sensors 272. In one embodiment, data from these sensors may be integrated with the data from the sensors in the body-worn device 210 and/or calculated by the body-worn device 210. In one embodiment, if computing device is also a user-carried device (e.g. a smart phone or similar format), the sensors 272 may include radiation sensor, motion sensor, and other sensors.

Computing system 250 may further include third party data connection 270. Third party data connection 270 may enable computing system 250 to obtain additional data, such as weather data, or other data that may be relevant to the calculations, from third parties. Such third parties may include general websites, dedicated data sources, etc.

Server system 275 includes server communicator 280, which enables server 275 to receive data from computing system 250 and/or body-worn device 210. Server 275 includes third party logic 282. In one embodiment, third party logic 282 provides statistical data, health or research data, as well as current information to server system 275. Calculation system 284 enables server system 275 to provide calculation assistance to the body-worn device 210 and/or computing system 250. In one embodiment, more complex calculations, such as adjustments due to user characteristics, are calculated on server system 275, or computing system 250.

Database 286, in one embodiment, maintains cumulative data from users. This may be used, in one embodiment, by statistical system 288 to adjust recommendations. Potentially, the data may also be made available to researchers, which may provide them useful information on user behavior, and correlative results based on user behavior. In one embodiment, server system 275 stores only statistical data, so that the user's personal data is not exposed. Alternatively, server system 275 may store personal data separately from statistical data, and make only statistical data available to third parties.

While these logics were shown in various locations, the actual systems that host each logic may differ. For example, in one embodiment, body-worn device 210 may simply include a radiation sensor 211, memory 242, and communications logic 238. In that embodiment, computing system 250 and/or server system 275 may provide the additional sensors and processors to make the calculations needed for the functionality described below. In one embodiment, the body-worn device 210 may function by itself, including a processor, with all additional features described with respect to computing system 250 and server 275 either absent or incorporated into the body-worn device 210. Other modifications from the above exemplary implementation may be made.

Figure 3:
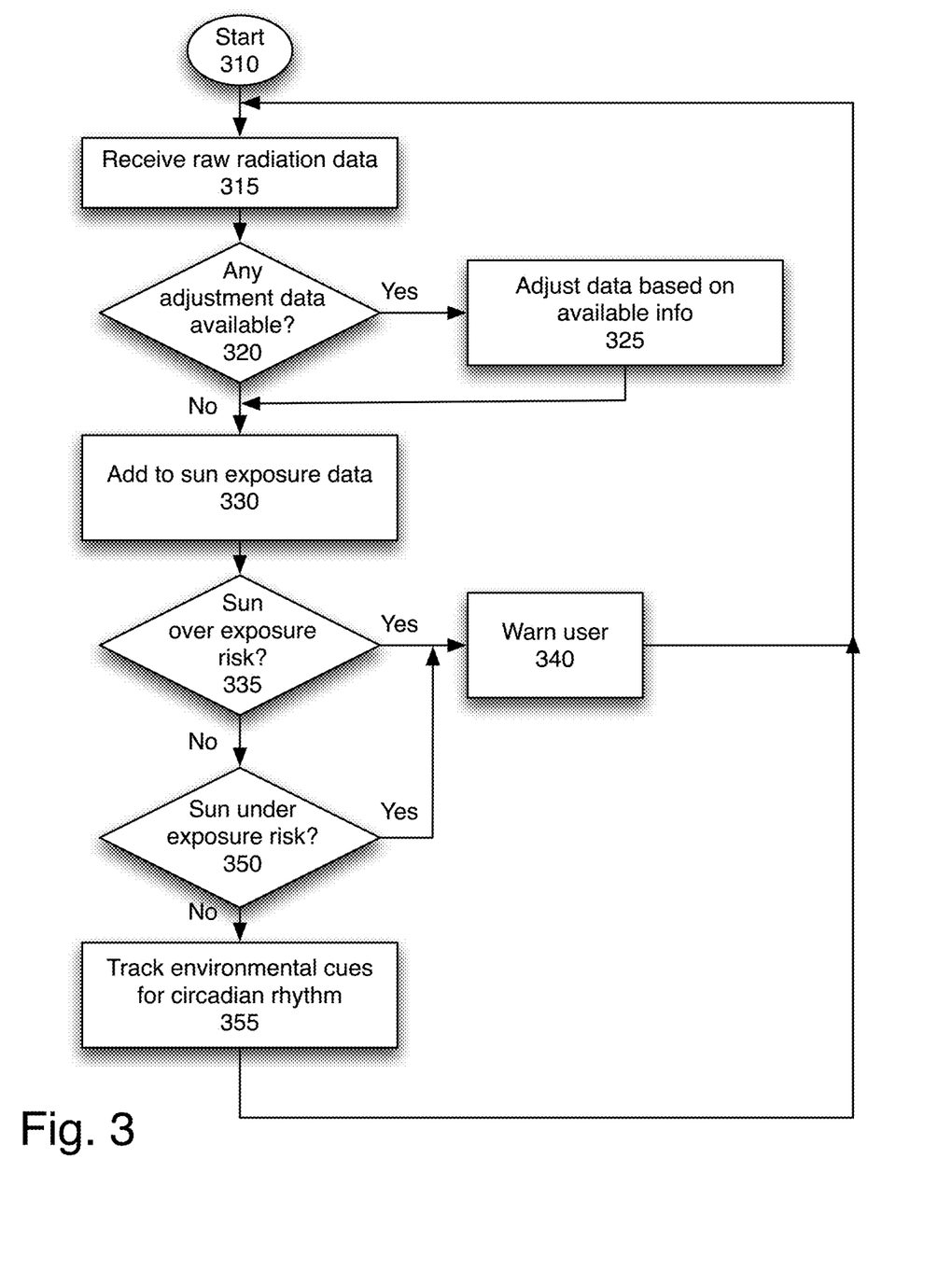
FIG. 3 is an overview flowchart of one embodiment of using the body-worn device.

FIG. 3 is a flowchart of one embodiment of using a sensor in the body-worn device. The process starts at block 310. In one embodiment, this process may be active whenever the radiation sensor detects radiation data. In one embodiment, the sensor differentiates between natural light and light from artificial light sources. Artificial light sources is general include fluorescent bulbs, traditional incandescent bulbs, or similar lights. The artificial light sources generally do not include UV-A or UV-B radiation. If a bulb does provide UV-A and/or UV-B radiation, in one embodiment the radiation sensor can, and should track exposure.

At block 315, the system receives raw radiation data. Raw radiation data identifies the UV-A, UV-B, and other relevant radiation levels, in one embodiment. The radiation level may be obtained by one or more UV radiation sensors. In another embodiment, the raw radiation level may be obtained from a light sensor, or different sensor, based on the measured data and additional calculations. Note that although the term "raw" is used, this does not imply that there is no processing in this step.

At block 320, the process determines whether there is any reason to adjust the raw radiation data. Reasons that may cause an adjustment include information about the user's characteristics, the user's current context, or other information.

If there is a reason to adjust, at block 325, the raw radiation data is adjusted in accordance with the available information, to produce effective exposure data. The process then continues to block 330. If there is no information causing an adjustment, the process continues directly to block 330.

At block 330, the effective exposure data is added to the cumulative total. In one embodiment, the system maintains a daily, weekly, and/or longer term totals of sun exposure. In general, sun exposure risk and benefit are cumulative. Therefore, cumulative data is maintained, and used to evaluate sun exposure, inform the user, and make recommendations.

At block 335, the process determines whether there is a sun over-exposure risk. Sun over-exposure risk may be sunburn, eye damage, increased cancer risk, wrinkles, or other harm to the body.

If there is a risk, at block 340 the user is warned. In one embodiment, the user may be warned through a user interface mechanism. In one embodiment, the user may be warned through a message sent to another device, such as an SMS or MMS sent to a cellular phone or an email sent to a email address. The process then returns to block 315, to continue receiving raw radiation data. In one embodiment, this process continues whenever radiation data is being received.

If there is no sun over-exposure risk, at block 335, the process continues to block 350. At block 350, the process determines whether there is a sun underexposure risk. Lack of sun exposure can lead to Vitamin D deficiency, depression, sleep disturbance, and potentially other problems. If there is a potential sun under-exposure risk, the process continues to block 340 to warn the user. The process then returns to block 315, to continue receiving raw radiation data.

If there is no sun underexposure risk, the process continues to block 355. At block 355, the system tracks environmental cues for circadian rhythm data. In one embodiment, the user may be informed of the result of this tracking. In one embodiment, this data may be used to adjust sleep reminders and alarms.

The process continues to block 315, where it continues to receive raw radiation data. While the system is described as flowcharts, in one embodiment the system continuously monitors all of the measurements, and compares them continuously to the risk factors described. In addition to sending timely alerts, in one embodiment the system maintains statistics available to the user. In one embodiment, the system may also send statistical data to a server.

In one embodiment, the user may control whether the sensors are active. In one embodiment, the system determines whether exposure data needs to be monitored on a periodic basis. In one embodiment, when a sensor indicates that the body-worn device being worn, the radiation sensor system is utilized. In one embodiment, when a measurement indicates that the body-worn device is inside a building with artificial light that does not include UV-A/UV-B radiation, the sensors may be temporarily turned off for power savings. In one embodiment, the sensors may be turned on again when the body-worn device has been moved, as indicated by the motion sensors. In one embodiment, a default use is to turn on sensors periodically to monitor motion, and to turn on radiation sensors at a first time interval if the prior measurement indicated sun exposure, at a second slower interval if the prior measurement indicated no sun exposure. In one embodiment, when the body-worn device is being worn and in the sun, the radiation sensor is turned on continuously.

Figure 4:
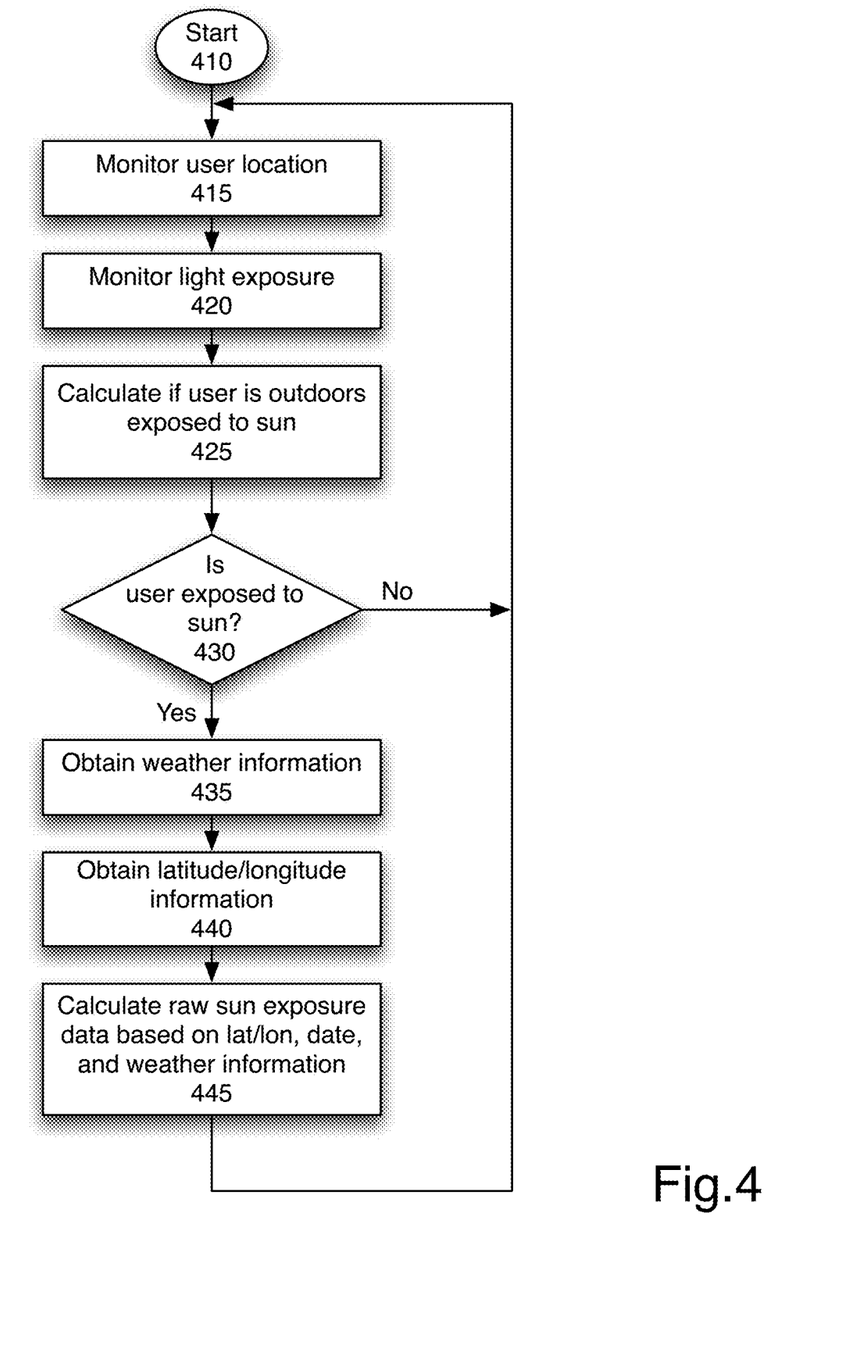
FIG. 4 is a flowchart of one embodiment of generating the raw radiation data.

FIG. 4 is a flowchart of one embodiment of generating the raw radiation data without a UV radiation detector. The process starts at block 410. The system may use a light exposure detector. This may make the radiation exposure evaluation, and recommendations, described available in older devices that do not include a radiation detector.

At block 415, the user's location is monitored, in one embodiment. Location data can be used to determine whether the user is inside, or outside, whether the user is in a shaded area or a sunny area, etc. In one embodiment, the location monitoring may occur through using GPS, network location sensing, cellular network triangulation, or other methods. In one embodiment, the system may further determine whether the user is inside or outside. In many cases, GPS signals are attenuated by going through walls or windows. In one embodiment, signal attenuation may be used to determine whether the user is inside or outside.

At block 420, the light exposure is monitored, in one embodiment. The light exposure data provides information about whether the user is in sunlight. In one embodiment, the light exposure data, in combination with additional information obtained based on location and time data is used to estimate exposure levels.

At block 425, the process calculates whether the user is outdoors, exposed to the sunlight or not. In one embodiment, additional data may be used to make this determination. Such additional data may include user motion data, temperature data, location data, and other sensor data.

At block 430, the process determines whether the user was being exposed to the sun. If the user is not being exposed, the process continues to block 415, to continue monitoring the user's location and light exposure.

If the user is being currently exposed to sun, at block 435, the process obtains weather information, if available. The process also calculates latitude/longitude information, based on the location data, at block 440.

Based on the location, weather, latitude/longitude, the process, at block 445 calculates a raw sun exposure. The raw sun exposure provides an estimate of the UV radiation. When weather, location, and latitude/longitude are taken into effect, a good estimate of current sunlight exposure can be created. In one embodiment, the raw sun exposure data is further processed, as discussed above with respect to FIG. 3. The process then returns to block 415 to continue monitoring location and exposure.

Figure 5A:
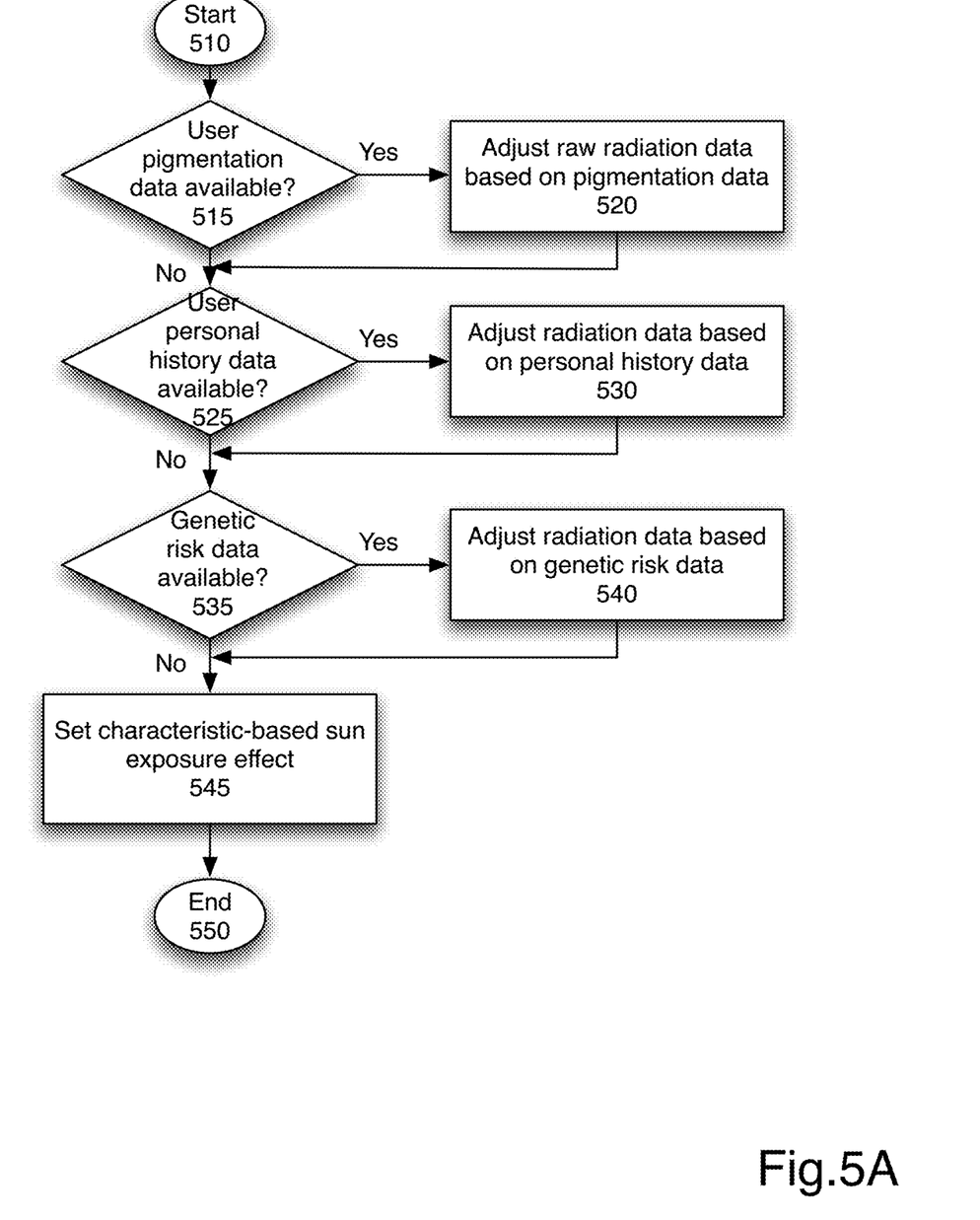
FIGS. 5A and 5B are flowcharts of embodiments of adjusting the raw radiation data.
Figure 5B:
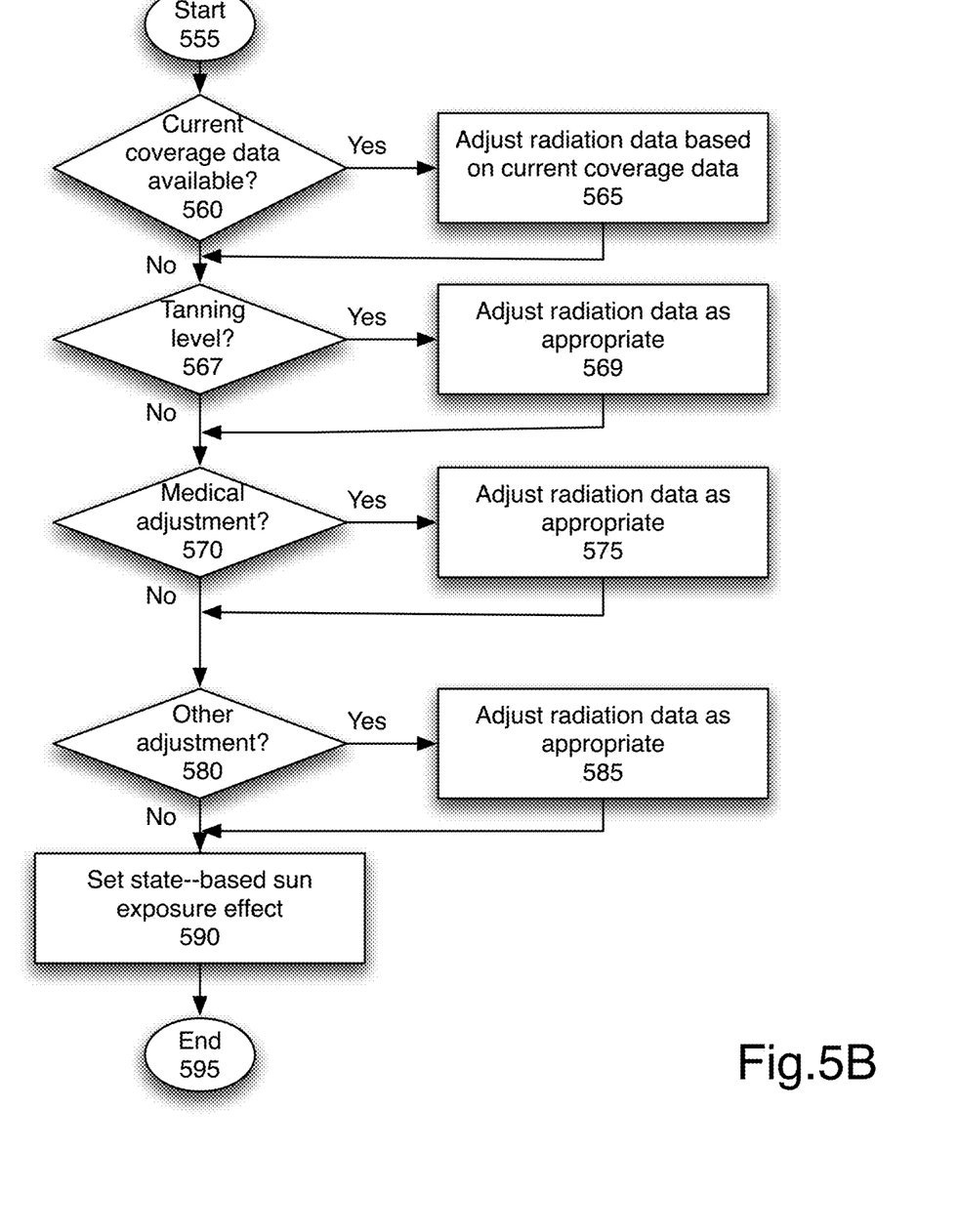

FIGS. 5A and 5B are flowcharts of one embodiment of adjusting the raw radiation data. The raw radiation data provides information of what level of radiation the body-worn device is absorbing, or the estimated raw exposure data calculated as described above with respect to FIG. 4. However, the impact of UV radiation is tempered by many factors. FIG. 5A illustrates one embodiment of the user characteristic-based factors, while FIG. 5B illustrates one embodiment of the user state-based factors.

FIG. 5A is a flowchart of one embodiment of calculating the user characteristic-based adjustments. The process starts at block 510. User characteristic adjustments may be done whenever additional user characteristic information is obtained, in one embodiment. Generally, user characteristics, and thus user characteristic adjustments, do not change.

Some of these factors may be based on user characteristics, e.g. user pigmentation (block 515), user personal history (block 525), genetic risk data (535). In one embodiment, the user may be asked to provide this type of data. In one embodiment, some of this data may be determined based on available information, e.g. from medical data provided by the user or released by a doctor with the user's authorization, from photographs of the user, or from publicly available information.

Genetic risk data, for example, may be based on genetic data enter by the user, released by the user from third parties such as doctors or testing agencies, or estimated based on circumstantial data. Circumstantial data, in one embodiment, may include the user's country of origin, or other such data. The adjustment for genetic risk, at block 540, uses known in the art adjustment factors. Similarly, pigmentation data may be obtained from self-portraits or photographs of the user, manually entered data, etc. The adjustments for skin pigmentation, at block 520, are based on known in the art relative absorption of UV-A and UV-B radiation based on skin tone.

Other user characteristics may be used to adjust radiation risk data as well. The user's personal history, either directly entered by the user or obtained with authorization from the user through third parties, also influences the risk factors associated with radiation exposure. For example, someone with prior history of melanoma is known to have a higher risk for skin cancer than someone without such a history. These types of correlations, as known now or determined in the future, are used, at block 530, to adjust the effect of the radiation data.

Additional user characteristics, which may be determined to be relevant may also be considered. In one embodiment, such characteristics may include family health data, as well as other relevant characteristics that may influence the user's reaction to sun exposure.

At block 545, the system sets the user characteristic-based adjustment. In one embodiment, the adjustment is a multiplier of the exposure level, e.g. characteristic-based exposure is evaluated as 1.4× raw exposure, to account for the user's red hair and fair skin. In another embodiment, the adjustment is an alteration of thresholds for certain alerts, e.g. the alert for excess exposure is lowered to account for the user's red hair and fair skin.

The process then ends at block 550. In one embodiment, whenever new personal data is added to the system, the user-characteristic-based adjustment may be recalculated or updated.

In addition to user characteristics, the current user state may also influence the impact of UV radiation. FIG. 5B is a flowchart illustrating one embodiment of that adjustment. The process starts at block 555. Current user state may include coverage data (block 560). Coverage includes, in one embodiment, sunscreen or clothing which may block UV radiation absorption. In one embodiment, this data may be entered by the user. In one embodiment, the user may take a picture or otherwise provide information about their current level of coverage. In one embodiment, there may be a switch or button indicating whether the user is wearing sunscreen, e.g. the user may alter the setting simply. The coverage data adjustment is performed at block 565.

In one embodiment, the user's tanning level also may influence how much effect sun exposure has. Once the skin has become darker from tanning, the activated melanin in the skin reduces the effect of further sun exposure. At block 567, the process determines whether there should be a tanning adjustment, and if so, the adjustment is made at 569.

In one embodiment, medications being taken may also influence the current effect of radiation on the user. For example, it is known that taking St. John's Wort increases photosensitivity, which may increase the likelihood of sunburn, and reduces sun tolerance in adults. At block 570, the system determines whether a medical adjustment is needed, and if so, the adjustment is made at block 575.

In one embodiment, additional adjustments (block 580) may be made, based on other data. When such data is available, it may also be taken into effect at block 585. As additional information is discovered about factors that may impact the user's radiation response, these adjustments may be made to the formula calculating effective sun exposure.

At block 590, the effective sun exposure is calculated, based on the raw sun exposure as adjusted by state-based, and optionally user characteristic based, adjustment. The process then ends, at block 595.

In one embodiment, calculations for user characteristic and user state adjustments may be made by a computer system or server, rather than by the body-worn device. In one embodiment, the adjustment calculations for user characteristics are done rarely, e.g. when the user initially sets up the system, or when additional user characteristic data is added into the system. In one embodiment, an adjustment factor may be created, based on the user characteristic data. For example, sun exposure may be multiplied by 1.2 to calculate the effective sun exposure for someone with a particular characteristic set. Alternatively, thresholds for certain conditions (e.g. sunburn, Vitamin D absorption) may be adjusted based on the user characteristic data. The body-worn device may store and utilize the adjustment factor, which is calculated by an external system, such as the computer system or server system discussed above.

Figure 6:
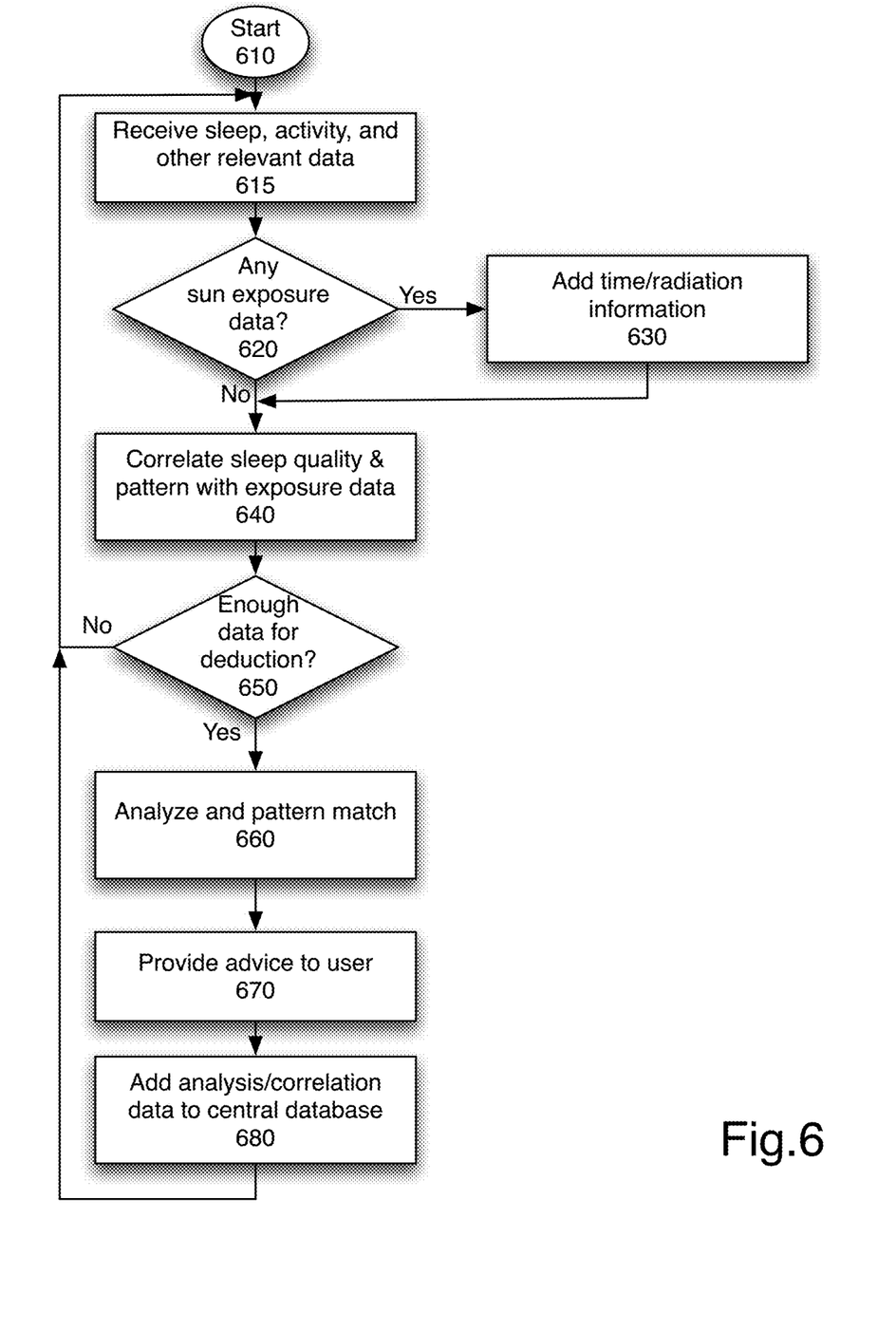
FIG. 6 is a flowchart of one embodiment of circadian rhythm analysis based on the radiation data.

FIG. 6 is a flowchart of one embodiment of circadian rhythm analysis based on the radiation data. The process starts at block 610. In one embodiment, the circadian rhythm calculation is done periodically. In one embodiment, it is done on a computer system or server, rather than on the body-worn device.

At block 615, sleep, activity, and other data relevant to the user's sleep pattern is received. The user's sleep pattern is defined by when the user sleeps, including the time the user goes to sleep, the number of sleep cycles, and the time the user wakes up, for each episode of sleep. In one embodiment, sleep information is obtained from the user, and/or from motion sensing. In one embodiment, sleep information includes the timing, length, and quality of sleep, overnight as well as any naps. In one embodiment, additional information may include local time, any changes in time zone, weather, and any other information which may impact the user's ability to sleep. As noted above, in one embodiment, the methods described with respect to U.S. application Ser. No. 13/545,963 may be used to determine sleep information.

At block 620, the process determines whether sun exposure data is available. If so, at block 630, the sun exposure data is added to the set of information that may be used to evaluate the user's sleep patterns. The production of melatonin is influenced by sunlight, and melatonin-based sleep adjustment and circadian rhythm adjustment may be used.

At block 640, the sleep quality and pattern is correlated with the sun exposure data pattern, and other relevant sensor data or external data.

At block 650, the process determines whether there is enough data to make any predictions. In one embodiment, there must be enough data to generate a pattern in order to make any predictions or recommendations. If there is not yet enough data, the process returns to block 615, to continue collecting data.

If there is enough data, at block 660, the process analyzes the information and attempts to pattern match the information.

At block 670, advice is provided to the user, if successfully deduced. The advice may be to get more sun, get less sun, get sun at a different time of day, add activity, or time shift activity. Potentially, recommendations may also include going to sleep at a different time, taking naps at a different time, lowering or raising temperatures, or other relevant recommendations deduced based on the user's sleep pattern and tracked sensor data. In one embodiment, the system may recommend adjustments to alarm times, as well as times when the user is outside taking in the sun or exercising.

At block 680, the analysis/correlation information is added to a central database in one embodiment. On one embodiment, any data added to the central database is scrubbed to remove any personal information. Patterns may develop over time, with a large number of users, which may be used to refine the recommendations of the system. For example, the system may observe, based on significant numbers of users, that sun exposure at a certain time, at a certain latitude, results in users sleeping better. This may be incorporated into the recommendation system.

Figure 7:
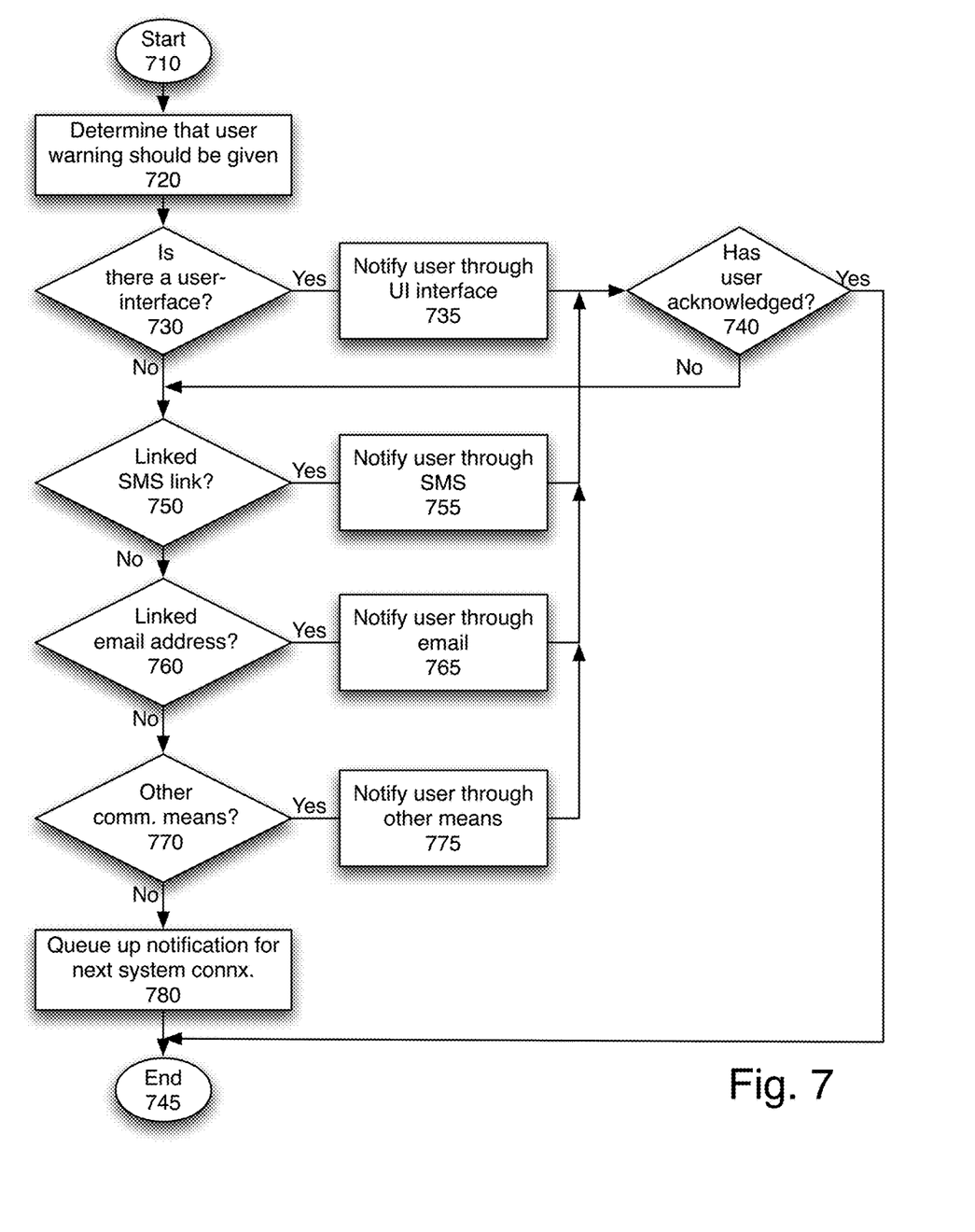
FIG. 7 is a flowchart of one embodiment of a warning system, which may be used with the present invention.

FIG. 7 is a flowchart of one embodiment of a warning system, which may be used with the present invention. The process starts at block 710. At block 720, the process determines that a user warning should be given. This may be due to an overexposure, an underexposure, or a recommended activity for the user.

At block 730, the process determines whether the body-worn device includes a user interface output. This may include a speaker, a light emitting diode (LED), a screen such as a liquid crystal display, e-ink screen, OLED, or other output. If such output is available, at block 735, the user is notified using the available UI feature.

At block 740, the process determines whether the user has acknowledged the notification. In on embodiment, if no user notification is received, an alternative notification method is added. In one embodiment, user acknowledgement may be an interaction or an action. For example, if the user notification is a request to be more active, and the user becomes more active, that may be taken as acknowledgement. If the user has acknowledged the notification, the process ends at block 745. Otherwise, the process continues to block 750, in one embodiment.

If there is no direct user interface that can be used for notification, the process continues directly to block 750.

At block 750, the process determines whether there is a linked mobile telephone. If there is a linked mobile number, in one embodiment, the system sends an SMS (short message system) message, MMS (multimedia messaging system), recorded audio message, or other type of alert to the mobile telephone, at block 755. The process then ends. If there is no linked mobile number, the process continues to block 760.

At block 760, the process determines whether there is a linked email address. If there is a linked email address, the system sends an email message notification, at block 765. The process then ends. If there is no linked mobile number, the process continues to block 770.

At block 770, the process determines whether there is another communication method. If so, at block 775, the user is sent a communication via the defined method. If there are no communication methods, at block 780, the process queues up a notification, for the next time the body-worn device is interfaced to another computer system, such as the local system or the server. The process then ends, at block 745.

Figure 8:
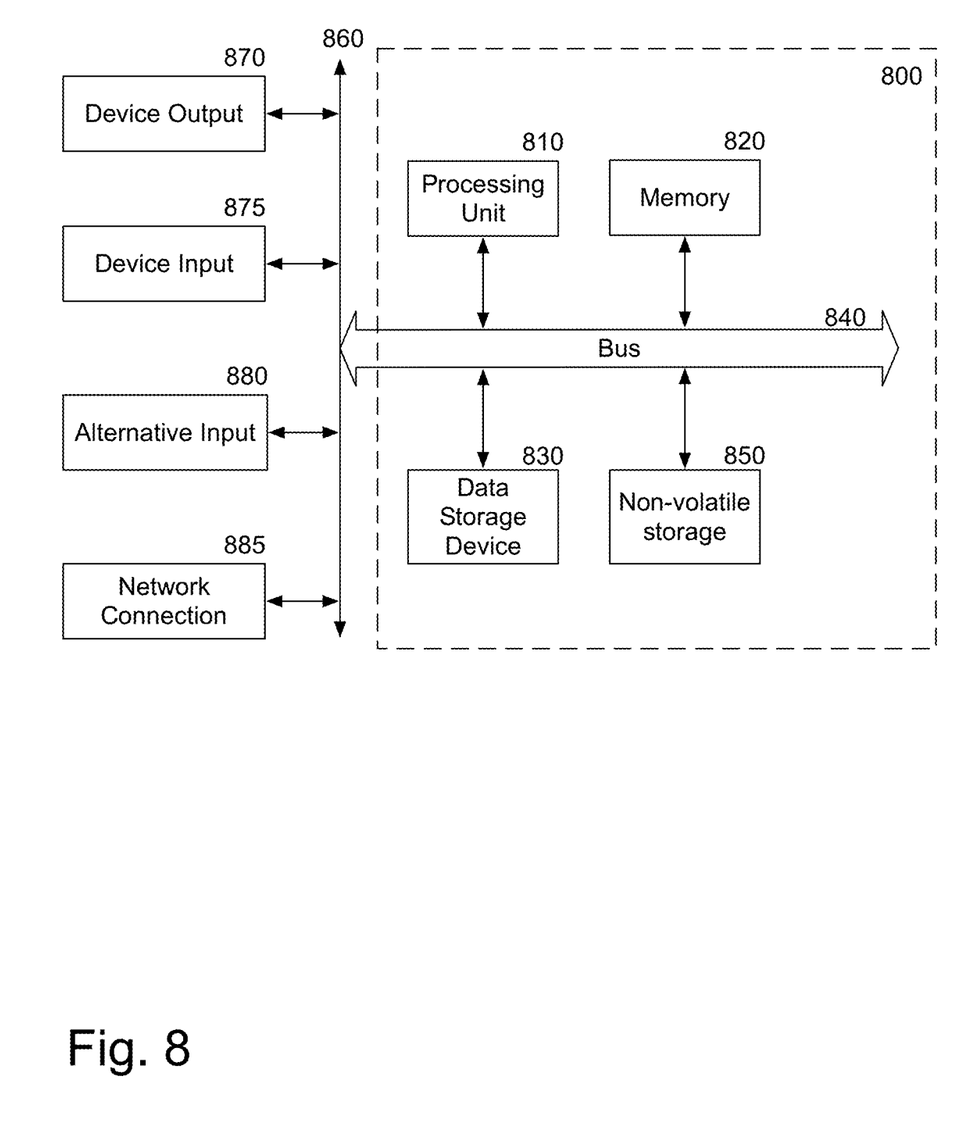
FIG. 8 is a computer system, which may be used with the present invention.

FIG. 8 is a computer system, which may be used with the present invention. It will be apparent to those of ordinary skill in the art, however that other alternative systems of various system architectures may also be used.

The data processing system illustrated in FIG. 8 includes a bus or other internal communication means 840 for communicating information, and a processing unit 810 coupled to the bus 840 for processing information. The processing unit 810 may be a central processing unit (CPU), a digital signal processor (DSP), or another type of processing unit 810.

The system further includes, in one embodiment, a random access memory (RAM) or other volatile storage device 820 (referred to as memory), coupled to bus 840 for storing information and instructions to be executed by processor 810. Main memory 820 may also be used for storing temporary variables or other intermediate information during execution of instructions by processing unit 810.

The system also comprises in one embodiment a read only memory (ROM) 850 and/or static storage device 850 coupled to bus 840 for storing static information and instructions for processor 810. In one embodiment the system also includes a data storage device 830 such as a magnetic disk or optical disk and its corresponding disk drive, or Flash memory or other storage which is capable of storing data when no power is supplied to the system. Data storage device 830 in one embodiment is coupled to bus 840 for storing information and instructions.

The system may further be coupled to an output device 870, such as a cathode ray tube (CRT) or a liquid crystal display (LCD) coupled to bus 840 through bus 860 for outputting information. The output device 870 may be a visual output device, an audio output device, and/or tactile output device (e.g. vibrations, etc.).

An input device 875 may be coupled to the bus 860. The input device 875 may be an alphanumeric input device, such as a keyboard including alphanumeric and other keys, for enabling a user to communicate information and command selections to processing unit 810. An additional user input device 880 may further be included. One such user input device 880 is cursor control device 880, such as a mouse, a trackball, stylus, cursor direction keys, or touch screen, may be coupled to bus 840 through bus 860 for communicating direction information and command selections to processing unit 810, and for controlling movement on display device 870.

Another device, which may optionally be coupled to computer system 800, is a network device 885 for accessing other nodes of a distributed system via a network. The communication device 885 may include any of a number of commercially available networking peripheral devices such as those used for coupling to an Ethernet, token ring, Internet, or wide area network, personal area network, wireless network or other method of accessing other devices. The communication device 885 may further be a null-modem connection, or any other mechanism that provides connectivity between the computer system 800 and the outside world.

Note that any or all of the components of this system illustrated in FIG. 8 and associated hardware may be used in various embodiments of the present invention.

It will be appreciated by those of ordinary skill in the art that the particular machine which embodies the present invention may be configured in various ways according to the particular implementation. The control logic or software implementing the present invention can be stored in main memory 820, mass storage device 830, or other storage medium locally or remotely accessible to processor 810.

It will be apparent to those of ordinary skill in the art that the system, method, and process described herein can be implemented as software stored in main memory 820 or read only memory 850 and executed by processor 810. This control logic or software may also be resident on an article of manufacture comprising a computer readable medium having computer readable program code embodied therein and being readable by the mass storage device 830 and for causing the processor 810 to operate in accordance with the methods and teachings herein.

The present invention may also be embodied in a handheld or portable device containing a subset of the computer hardware components described above. For example, the handheld device may be configured to contain only the bus 815, the processor 810, and memory 850 and/or 820.

The handheld device may be configured to include a set of buttons or input signaling components with which a user may select from a set of available options. These could be considered input device #1 875 or input device #2 880. The handheld device may also be configured to include an output device 870 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processing unit 810, a data storage device 830, a bus 840, and memory 820, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 885.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 810. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A body-worn device, comprising:
    at least one radiation sensor detecting UV radiation, implemented in the body-worn device, that converts the detected UV radiation into UV radiation data, wherein a radiation sensor of the at least one radiation sensor differentiates between natural and artificial light;

at least one processor implementing:
- an exposure data calculator that receives the UV radiation data and adjusts the UV radiation data to determine an effective radiation exposure by applying a multiplier to the UV radiation data based on a combination of: a user state, user characteristics, and health history, the health history including prior health conditions;
- a recommendation calculator to determine a recommendation to the user, based on the effective radiation exposure;
- a motion sensor determining when the body-worn device is not being worn, wherein the at least one processor turns off the body-worn device, to save power; and
- a wireless connection mechanism wherein at least one of the user state, the user characteristics, and the health history, are accessed using the wireless connection mechanism.

2. The body-worn device of claim 1, wherein the processor further turns off the system when the body-worn device is not being exposed to the sunlight when a location of the user is determined as being indoors.

3. The body-worn device of claim 1, wherein the exposure data calculator adjusts the exposure based on one or more of: genetic risk data and personal medical history of the user.

4. The body-worn device of claim 1, wherein the at least one radiation sensor comprises a radiation calculation system including:
- a light exposure system to determine light exposure;
- a location calculator to determine a current location; and
- a weather adjustor to utilize weather data to adjust an exposure estimate; wherein the radiation calculation system provides an estimated raw radiation exposure without using a UV sensor.

5. The body-worn device of claim 1, wherein the at least one radiation sensor measures UV-A and UV-B radiation exposure.

6. The body-worn device of claim 1, further comprising:
- an interface to provide the recommendation to the user, wherein the interface comprises one of: an output on the body-worn device, and a communications system to send a message to the user with the recommendation.

7. The body-worn device of claim 6, wherein when a user does not acknowledge the output on the body-worn device, the communications system sends a follow-up message to the user.

8. The body-worn device of claim 1, further comprising:
- a communication to send cumulative data to a server system, to enable generation of statistical data.

9. The body-worn device of claim 1, wherein the user characteristics include one or more of country of origin, hair color, and skin tone, and the health history comprises one or more of: the user's prior history of skin cancer and family health data of the user's family.

10. A method, comprising:
- converting detected UV radiation into UV radiation data, wherein a radiation sensor of the at least one radiation sensor differentiates between natural and artificial light, by at least one radiation sensor detecting the UV radiation, implemented in a body-worn device;
- receiving the UV radiation data and adjusting, by a processor, the UV radiation data based on a combination of user characteristics, health history, and user state to generate an effective exposure;
- determining a cumulative effective exposure and providing, by a processor, a recommendation to a user based on the cumulative effective exposure;
- turning off the system when the body-worn device is not being worn, as determined by a motion sensor, and thus is not monitoring the sun exposure data of the user to save power; and
- accessing at least one of the user state, the user characteristics, and the health history using the wireless connection mechanism.

11. The method of claim 10, wherein the recommendation comprises one or more of: getting more sun, getting less sun, shifting a time when sun exposure is experienced.

12. The method of claim 11, wherein the recommendation is designed to help the user avoid risking a combination of: Vitamin D deficiency, sunburn, tanning, and wrinkles, or adjust the user's circadian rhythm.

* * * * *